US012805928B2

(12) United States Patent
Govari et al.

(10) Patent No.: US 12,805,928 B2
(45) Date of Patent: Nov. 24, 2026

(54) CATHETER AND TISSUE USING TRANSMITTER AND RECEIVERS OF THE CATHETER

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Andres Claudio Altmann, Haifa (IL); Vadim Gliner, Haifa (IL); Joseph Thomas Keyes, Sierra Madre, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 881 days.

(21) Appl. No.: 17/523,155

(22) Filed: Nov. 10, 2021

(65) Prior Publication Data

US 2023/0147259 A1 May 11, 2023

(51) Int. Cl.

| | |
|---|---|
| ***A61B 18/14*** | (2006.01) |
| ***A61B 18/00*** | (2006.01) |
| ***A61B 90/00*** | (2016.01) |

(52) U.S. Cl.

CPC .......... *A61B 18/1492* (2013.01); *A61B 90/06* (2016.02); *A61B 2018/0022* (2013.01); *A61B 2018/00267* (2013.01); *A61B 2018/00577* (2013.01); *A61B 2090/065* (2016.02)

(58) Field of Classification Search

CPC ................ A61B 18/1492; A61B 90/06; A61B 2018/00267; A61B 2018/00577; A61B 2018/00214; A61B 2018/0022; A61B 2090/065

See application file for complete search history.

(56) References Cited

U.S. PATENT DOCUMENTS

| | | | |
|---|---|---|---|
| 4,699,147 | A | 10/1987 | Chilson et al. |
| 4,940,064 | A | 7/1990 | Desai |
| 5,215,103 | A | 6/1993 | Desai |
| 5,255,679 | A | 10/1993 | Imran |
| 5,293,869 | A | 3/1994 | Edwards et al. |
| 5,309,910 | A | 5/1994 | Edwards et al. |

(Continued)

FOREIGN PATENT DOCUMENTS

| | | | |
|---|---|---|---|
| CN | 111248993 | A | 6/2020 |
| CN | 111248996 | A | 6/2020 |

(Continued)

OTHER PUBLICATIONS

Extended European Search Report and Search Opinion dated Mar. 24, 2023, from corresponding European Application No. 22206307.5.

(Continued)

*Primary Examiner* — Annie L Shoulders

(57) ABSTRACT

A system includes a catheter and a processor. The catheter includes an expandable distal-end assembly (EDEA) having: (i) a transmitter, which is coupled to the EDEA and is configured to transmit a first signal, and (ii) one or more receivers, which are coupled to an elastic component of the EDEA, and are configured to produce one or more respective second signals in response to receiving the first signal. The processor is configured to estimate, based on the one or more respective second signals, a force applied to the elastic component.

13 Claims, 2 Drawing Sheets

(56) References Cited

U.S. PATENT DOCUMENTS

| | | | |
|---|---|---|---|
| 5,313,943 | A | 5/1994 | Houser et al. |
| 5,324,284 | A | 6/1994 | Imran |
| 5,345,936 | A | 9/1994 | Pomeranz et al. |
| 5,365,926 | A | 11/1994 | Desai |
| 5,391,199 | A | 2/1995 | Ben-Haim |
| 5,396,887 | A | 3/1995 | Imran |
| 5,400,783 | A | 3/1995 | Pomeranz et al. |
| 5,411,025 | A | 5/1995 | Webster, Jr. |
| 5,415,166 | A | 5/1995 | Imran |
| 5,456,254 | A | 10/1995 | Pietroski et al. |
| 5,465,717 | A | 11/1995 | Imran et al. |
| 5,476,495 | A | 12/1995 | Kordis et al. |
| 5,499,981 | A | 3/1996 | Kordis |
| 5,526,810 | A | 6/1996 | Wang |
| 5,546,940 | A | 8/1996 | Panescu et al. |
| 5,549,108 | A | 8/1996 | Edwards et al. |
| 5,558,073 | A | 9/1996 | Pomeranz et al. |
| 5,577,509 | A | 11/1996 | Panescu et al. |
| 5,595,183 | A | 1/1997 | Swanson et al. |
| 5,598,848 | A | 2/1997 | Swanson et al. |
| 5,609,157 | A | 3/1997 | Panescu et al. |
| 5,628,313 | A | 5/1997 | Webster, Jr. |
| 5,681,280 | A | 10/1997 | Rusk et al. |
| 5,722,401 | A | 3/1998 | Pietroski et al. |
| 5,722,403 | A | 3/1998 | McGee et al. |
| 5,725,525 | A | 3/1998 | Kordis |
| 5,730,128 | A | 3/1998 | Pomeranz et al. |
| 5,772,590 | A | 6/1998 | Webster, Jr. |
| 5,782,899 | A | 7/1998 | Imran |
| 5,823,189 | A | 10/1998 | Kordis |
| 5,881,727 | A | 3/1999 | Edwards |
| 5,893,847 | A | 4/1999 | Kordis |
| 5,904,680 | A | 5/1999 | Kordis et al. |
| 5,911,739 | A | 6/1999 | Kordis et al. |
| 5,928,228 | A | 7/1999 | Kordis et al. |
| 5,968,040 | A | 10/1999 | Swanson et al. |
| 6,014,579 | A | 1/2000 | Pomeranz et al. |
| 6,014,590 | A | 1/2000 | Whayne et al. |
| 6,119,030 | A | 9/2000 | Morency |
| 6,142,993 | A | 11/2000 | Whayne et al. |
| 6,216,043 | B1 | 4/2001 | Swanson et al. |
| 6,216,044 | B1 | 4/2001 | Kordis |
| 6,239,724 | B1 | 5/2001 | Doron et al. |
| 6,332,089 | B1 | 12/2001 | Acker et al. |
| 6,428,537 | B1 | 8/2002 | Swanson et al. |
| 6,456,864 | B1 | 9/2002 | Swanson et al. |
| 6,484,118 | B1 | 11/2002 | Govari |
| 6,574,492 | B1 | 6/2003 | Ben-Haim et al. |
| 6,584,345 | B2 | 6/2003 | Govari |
| 6,600,948 | B2 | 7/2003 | Ben-Haim et al. |
| 6,618,612 | B1 | 9/2003 | Acker et al. |
| 6,690,963 | B2 | 2/2004 | Ben-Haim et al. |
| 6,738,655 | B1 | 5/2004 | Sen et al. |
| 6,741,878 | B2 | 5/2004 | Fuimaono et al. |
| 6,748,255 | B2 | 6/2004 | Fuimaono et al. |
| 6,780,183 | B2 | 8/2004 | Jimenez, Jr. et al. |
| 6,837,886 | B2 | 1/2005 | Collins et al. |
| 6,866,662 | B2 | 3/2005 | Fuimaono et al. |
| 6,892,091 | B1 | 5/2005 | Ben-Haim et al. |
| 6,970,730 | B2 | 11/2005 | Fuimaono et al. |
| 6,973,340 | B2 | 12/2005 | Fuimaono et al. |
| 6,980,858 | B2 | 12/2005 | Fuimaono et al. |
| 7,048,734 | B1 | 5/2006 | Fleischman et al. |
| 7,149,563 | B2 | 12/2006 | Fuimaono et al. |
| 7,255,695 | B2 | 8/2007 | Falwell et al. |
| 7,257,434 | B2 | 8/2007 | Fuimaono et al. |
| 7,399,299 | B2 | 7/2008 | Daniel et al. |
| 7,410,486 | B2 | 8/2008 | Fuimaono et al. |
| 7,522,950 | B2 | 4/2009 | Fuimaono et al. |
| RE41,334 | E | 5/2010 | Beatty et al. |
| 7,846,157 | B2 | 12/2010 | Kozel |
| 7,930,018 | B2 | 4/2011 | Harlev et al. |
| 8,007,495 | B2 | 8/2011 | McDaniel et al. |
| 8,048,063 | B2 | 11/2011 | Aeby et al. |
| 8,103,327 | B2 | 1/2012 | Harlev et al. |
| 8,167,845 | B2 | 5/2012 | Wang et al. |
| 8,224,416 | B2 | 7/2012 | De La Rama et al. |
| 8,235,988 | B2 | 8/2012 | Davis et al. |
| 8,346,339 | B2 | 1/2013 | Kordis et al. |
| 8,435,232 | B2 | 5/2013 | Aeby et al. |
| 8,447,377 | B2 | 5/2013 | Harlev et al. |
| 8,498,686 | B2 | 7/2013 | Grunewald |
| 8,517,999 | B2 | 8/2013 | Pappone et al. |
| 8,545,490 | B2 | 10/2013 | Mihajlovic et al. |
| 8,560,086 | B2 | 10/2013 | Just et al. |
| 8,567,265 | B2 | 10/2013 | Aeby et al. |
| 8,712,550 | B2 | 4/2014 | Grunewald |
| 8,755,861 | B2 | 6/2014 | Harlev et al. |
| 8,825,130 | B2 | 9/2014 | Just et al. |
| 8,906,011 | B2 | 12/2014 | Gelbart et al. |
| 8,945,120 | B2 | 2/2015 | McDaniel et al. |
| 8,979,839 | B2 | 3/2015 | De La Rama et al. |
| 9,037,264 | B2 | 5/2015 | Just et al. |
| 9,060,756 | B2 | 6/2015 | Bencini |
| 9,131,980 | B2 | 9/2015 | Bloom |
| 9,204,929 | B2 | 12/2015 | Solis |
| 9,277,960 | B2 | 3/2016 | Weinkam et al. |
| 9,314,208 | B1 | 4/2016 | Altmann et al. |
| 9,339,331 | B2 | 5/2016 | Tegg et al. |
| 9,474,486 | B2 | 10/2016 | Eliason |
| 9,486,282 | B2 | 11/2016 | Solis |
| 9,554,718 | B2 | 1/2017 | Bar-Tal et al. |
| D782,686 | S | 3/2017 | Werneth et al. |
| 9,585,588 | B2 | 3/2017 | Marecki et al. |
| 9,597,036 | B2 | 3/2017 | Aeby et al. |
| 9,687,297 | B2 | 6/2017 | Just et al. |
| 9,693,733 | B2 | 7/2017 | Altmann et al. |
| 9,757,180 | B2 | 9/2017 | Gelfand |
| 9,782,099 | B2 | 10/2017 | Williams et al. |
| 9,788,895 | B2 | 10/2017 | Solis |
| 9,801,681 | B2 | 10/2017 | Laske et al. |
| 9,814,618 | B2 | 11/2017 | Nguyen et al. |
| 9,833,161 | B2 | 12/2017 | Govari |
| 9,894,756 | B2 | 2/2018 | Weinkam et al. |
| 9,895,073 | B2 | 2/2018 | Solis |
| 9,907,609 | B2 | 3/2018 | Cao et al. |
| 9,974,460 | B2 | 5/2018 | Wu et al. |
| 9,986,949 | B2 | 6/2018 | Govari et al. |
| 9,993,160 | B2 | 6/2018 | Salvestro et al. |
| 10,014,607 | B1 | 7/2018 | Govari et al. |
| 10,028,376 | B2 | 7/2018 | Weinkam et al. |
| 10,034,637 | B2 | 7/2018 | Harlev et al. |
| 10,039,494 | B2 | 8/2018 | Altmann et al. |
| 10,045,707 | B2 | 8/2018 | Govari |
| 10,078,713 | B2 | 9/2018 | Auerbach et al. |
| 10,111,623 | B2 | 10/2018 | Jung et al. |
| 10,130,420 | B2 | 11/2018 | Basu et al. |
| 10,136,828 | B2 | 11/2018 | Houben et al. |
| 10,143,394 | B2 | 12/2018 | Solis |
| 10,172,536 | B2 | 1/2019 | Maskara et al. |
| 10,182,762 | B2 | 1/2019 | Just et al. |
| 10,194,818 | B2 | 2/2019 | Williams et al. |
| 10,201,311 | B2 | 2/2019 | Chou et al. |
| 10,219,860 | B2 | 3/2019 | Harlev et al. |
| 10,219,861 | B2 | 3/2019 | Just et al. |
| 10,231,328 | B2 | 3/2019 | Weinkam et al. |
| 10,238,309 | B2 | 3/2019 | Bar-Tal et al. |
| 10,278,590 | B2 | 5/2019 | Salvestro et al. |
| D851,774 | S | 6/2019 | Werneth et al. |
| 10,314,505 | B2 | 6/2019 | Williams et al. |
| 10,314,507 | B2 | 6/2019 | Govari et al. |
| 10,314,648 | B2 | 6/2019 | Ge et al. |
| 10,314,649 | B2 | 6/2019 | Bakos et al. |
| 10,349,855 | B2 | 7/2019 | Zeidan et al. |
| 10,350,003 | B2 | 7/2019 | Weinkam et al. |
| 10,362,952 | B2 | 7/2019 | Basu |
| 10,362,991 | B2 | 7/2019 | Tran et al. |
| 10,375,827 | B2 | 8/2019 | Weinkam et al. |
| 10,376,170 | B2 | 8/2019 | Quinn et al. |
| 10,376,221 | B2 | 8/2019 | Iyun et al. |
| 10,398,348 | B2 | 9/2019 | Osadchy et al. |
| 10,403,053 | B2 | 9/2019 | Katz et al. |
| 10,441,188 | B2 | 10/2019 | Katz et al. |
| 10,470,682 | B2 | 11/2019 | Deno et al. |

(56) References Cited

U.S. PATENT DOCUMENTS

| | | | | |
|---|---|---|---|---|
| 10,470,714 | B2 | 11/2019 | Altmann et al. | |
| 10,482,198 | B2 | 11/2019 | Auerbach et al. | |
| 10,492,857 | B2 | 12/2019 | Guggenberger et al. | |
| 10,542,620 | B2 | 1/2020 | Weinkam et al. | |
| 10,575,743 | B2 | 3/2020 | Basu et al. | |
| 10,575,745 | B2 | 3/2020 | Solis | |
| 10,582,871 | B2 | 3/2020 | Williams et al. | |
| 10,582,894 | B2 | 3/2020 | Ben Zrihem et al. | |
| 10,596,346 | B2 | 3/2020 | Aeby et al. | |
| 10,602,947 | B2 | 3/2020 | Govari et al. | |
| 10,617,867 | B2 | 4/2020 | Viswanathan et al. | |
| 10,660,702 | B2 | 5/2020 | Viswanathan et al. | |
| 10,667,753 | B2 | 6/2020 | Werneth et al. | |
| 10,674,929 | B2 | 6/2020 | Houben et al. | |
| 10,681,805 | B2 | 6/2020 | Weinkam et al. | |
| 10,682,181 | B2 | 6/2020 | Cohen et al. | |
| 10,687,892 | B2 | 6/2020 | Long et al. | |
| 10,702,178 | B2 | 7/2020 | Dahlen et al. | |
| 10,716,477 | B2 | 7/2020 | Salvestro et al. | |
| 10,751,534 | B2 * | 8/2020 | Hiller | A61B 5/4283 |
| 10,758,304 | B2 | 9/2020 | Aujla | |
| 10,765,371 | B2 | 9/2020 | Hayam et al. | |
| 10,772,566 | B2 | 9/2020 | Aujila | |
| 10,799,281 | B2 * | 10/2020 | Goertzen | A61B 34/20 |
| 10,842,558 | B2 | 11/2020 | Harlev et al. | |
| 10,842,561 | B2 | 11/2020 | Viswanathan et al. | |
| 10,863,914 | B2 | 12/2020 | Govari et al. | |
| 10,881,376 | B2 | 1/2021 | Shemesh et al. | |
| 10,898,139 | B2 | 1/2021 | Guta et al. | |
| 10,905,329 | B2 | 2/2021 | Bar-Tal et al. | |
| 10,912,484 | B2 | 2/2021 | Ziv-Ari et al. | |
| 10,918,306 | B2 | 2/2021 | Govari et al. | |
| 10,939,871 | B2 | 3/2021 | Altmann et al. | |
| 10,952,795 | B2 | 3/2021 | Cohen et al. | |
| 10,973,426 | B2 | 4/2021 | Williams et al. | |
| 10,973,461 | B2 | 4/2021 | Baram et al. | |
| 10,987,045 | B2 | 4/2021 | Basu et al. | |
| 11,006,902 | B1 | 5/2021 | Bonyak et al. | |
| 11,040,208 | B1 | 6/2021 | Govari et al. | |
| 11,045,628 | B2 | 6/2021 | Beeckler et al. | |
| 11,051,877 | B2 | 7/2021 | Sliwa et al. | |
| 11,109,788 | B2 | 9/2021 | Rottmann et al. | |
| 11,116,435 | B2 | 9/2021 | Urman et al. | |
| 11,129,574 | B2 | 9/2021 | Cohen et al. | |
| 11,160,482 | B2 | 11/2021 | Solis | |
| 11,164,371 | B2 | 11/2021 | Yellin et al. | |
| 2002/0006455 | A1 | 1/2002 | Levine | |
| 2002/0065455 | A1 | 5/2002 | Ben-Haim et al. | |
| 2002/0198522 | A1 | 12/2002 | Kordis | |
| 2003/0120150 | A1 | 6/2003 | Govari | |
| 2004/0068178 | A1 | 4/2004 | Govari | |
| 2004/0210121 | A1 | 10/2004 | Fuimaono et al. | |
| 2005/0033285 | A1 | 2/2005 | Swanson et al. | |
| 2005/0096647 | A1 | 5/2005 | Steinke et al. | |
| 2006/0009689 | A1 | 1/2006 | Fuimaono et al. | |
| 2006/0009690 | A1 | 1/2006 | Fuimaono et al. | |
| 2006/0100669 | A1 | 5/2006 | Fuimaono et al. | |
| 2007/0093806 | A1 | 4/2007 | Desai et al. | |
| 2007/0276212 | A1 | 11/2007 | Fuimaono et al. | |
| 2008/0234564 | A1 | 9/2008 | Beatty et al. | |
| 2009/0093806 | A1 * | 4/2009 | Govari | A61B 18/1492 606/34 |
| 2009/0259274 | A1 | 10/2009 | Simon et al. | |
| 2011/0118726 | A1 | 5/2011 | De La Rama et al. | |
| 2011/0160574 | A1 | 6/2011 | Harlev et al. | |
| 2011/0190625 | A1 | 8/2011 | Harlev et al. | |
| 2011/0245756 | A1 | 10/2011 | Arora et al. | |
| 2011/0301597 | A1 | 12/2011 | McDaniel et al. | |
| 2012/0136350 | A1 | 5/2012 | Goshgarian et al. | |
| 2012/0271140 | A1 | 10/2012 | Kordis et al. | |
| 2012/0296232 | A1 * | 11/2012 | Ng | A61B 18/1492 600/554 |
| 2013/0085493 | A1 | 4/2013 | Bloom et al. | |
| 2013/0090651 | A1 | 4/2013 | Smith | |
| 2013/0172872 | A1 | 7/2013 | Subramaniam et al. | |
| 2013/0172883 | A1 | 7/2013 | Lopes et al. | |
| 2013/0178850 | A1 | 7/2013 | Lopes et al. | |
| 2013/0190587 | A1 | 7/2013 | Lopes et al. | |
| 2013/0197499 | A1 | 8/2013 | Lalonde et al. | |
| 2013/0296852 | A1 | 11/2013 | Madjarov et al. | |
| 2014/0025069 | A1 | 1/2014 | Willard et al. | |
| 2014/0031810 | A1 | 1/2014 | Mahvi et al. | |
| 2014/0052118 | A1 | 2/2014 | Laske et al. | |
| 2014/0180147 | A1 | 6/2014 | Thakur et al. | |
| 2014/0180151 | A1 | 6/2014 | Maskara et al. | |
| 2014/0180152 | A1 | 6/2014 | Maskara et al. | |
| 2014/0257069 | A1 | 9/2014 | Eliason et al. | |
| 2014/0276712 | A1 | 9/2014 | Mallin et al. | |
| 2014/0309512 | A1 | 10/2014 | Govari et al. | |
| 2015/0011991 | A1 | 1/2015 | Buysman et al. | |
| 2015/0025532 | A1 | 1/2015 | Hanson et al. | |
| 2015/0045863 | A1 | 2/2015 | Litscher et al. | |
| 2015/0080693 | A1 | 3/2015 | Solis | |
| 2015/0105770 | A1 | 4/2015 | Amit | |
| 2015/0119878 | A1 | 4/2015 | Heisel et al. | |
| 2015/0133919 | A1 | 5/2015 | McDaniel et al. | |
| 2015/0196740 | A1 | 7/2015 | Mallin et al. | |
| 2015/0208942 | A1 | 7/2015 | Bar-Tal et al. | |
| 2015/0250424 | A1 | 9/2015 | Govari et al. | |
| 2015/0270634 | A1 | 9/2015 | Buesseler et al. | |
| 2015/0342532 | A1 | 12/2015 | Basu et al. | |
| 2015/0351652 | A1 | 12/2015 | Marecki et al. | |
| 2016/0081746 | A1 | 3/2016 | Solis | |
| 2016/0113582 | A1 | 4/2016 | Altmann et al. | |
| 2016/0113709 | A1 | 4/2016 | Maor | |
| 2016/0183877 | A1 | 6/2016 | Williams et al. | |
| 2016/0228023 | A1 | 8/2016 | Govari | |
| 2016/0228062 | A1 | 8/2016 | Altmann et al. | |
| 2016/0278853 | A1 | 9/2016 | Ogle et al. | |
| 2016/0302858 | A1 | 10/2016 | Bencini | |
| 2016/0338770 | A1 | 11/2016 | Bar-Tal et al. | |
| 2017/0027638 | A1 | 2/2017 | Solis | |
| 2017/0035496 | A1 | 2/2017 | Nagale et al. | |
| 2017/0065227 | A1 | 3/2017 | Marrs et al. | |
| 2017/0071543 | A1 | 3/2017 | Basu et al. | |
| 2017/0071544 | A1 | 3/2017 | Basu et al. | |
| 2017/0071665 | A1 | 3/2017 | Solis | |
| 2017/0095173 | A1 | 4/2017 | Bar-Tal et al. | |
| 2017/0100187 | A1 | 4/2017 | Basu et al. | |
| 2017/0143227 | A1 | 5/2017 | Marecki et al. | |
| 2017/0156790 | A1 | 6/2017 | Aujla | |
| 2017/0164999 | A1 | 6/2017 | Hettel | |
| 2017/0172442 | A1 | 6/2017 | Govari | |
| 2017/0185702 | A1 | 6/2017 | Auerbach et al. | |
| 2017/0202515 | A1 | 7/2017 | Zrihem et al. | |
| 2017/0221262 | A1 | 8/2017 | Laughner et al. | |
| 2017/0224958 | A1 | 8/2017 | Cummings et al. | |
| 2017/0265812 | A1 | 9/2017 | Williams et al. | |
| 2017/0281031 | A1 | 10/2017 | Houben et al. | |
| 2017/0281268 | A1 | 10/2017 | Tran et al. | |
| 2017/0296125 | A1 | 10/2017 | Altmann et al. | |
| 2017/0296251 | A1 | 10/2017 | Wu et al. | |
| 2017/0312012 | A1 | 11/2017 | Harlev et al. | |
| 2017/0312420 | A1 | 11/2017 | Harlev et al. | |
| 2017/0347959 | A1 | 12/2017 | Guta et al. | |
| 2017/0348049 | A1 | 12/2017 | Vrba et al. | |
| 2017/0354338 | A1 | 12/2017 | Levin et al. | |
| 2017/0354339 | A1 | 12/2017 | Zeidan et al. | |
| 2017/0354364 | A1 | 12/2017 | Bar-Tal et al. | |
| 2018/0008203 | A1 | 1/2018 | Iyun et al. | |
| 2018/0028084 | A1 | 2/2018 | Williams et al. | |
| 2018/0049803 | A1 | 2/2018 | Solis | |
| 2018/0076336 | A1 | 3/2018 | DeGraff et al. | |
| 2018/0085064 | A1 | 3/2018 | Auerbach et al. | |
| 2018/0132749 | A1 | 5/2018 | Govari et al. | |
| 2018/0137687 | A1 | 5/2018 | Katz et al. | |
| 2018/0160936 | A1 | 6/2018 | Govari et al. | |
| 2018/0160978 | A1 | 6/2018 | Cohen et al. | |
| 2018/0161093 | A1 | 6/2018 | Basu et al. | |
| 2018/0168511 | A1 | 6/2018 | Hall et al. | |
| 2018/0184982 | A1 | 7/2018 | Basu et al. | |
| 2018/0192958 | A1 | 7/2018 | Wu | |
| 2018/0206792 | A1 | 7/2018 | Auerbach et al. | |
| 2018/0235692 | A1 | 8/2018 | Efimov et al. | |

(56) References Cited

U.S. PATENT DOCUMENTS

| | | | |
|---|---|---|---|
| 2018/0249959 | A1 | 9/2018 | Osypka |
| 2018/0256109 | A1 | 9/2018 | Wu et al. |
| 2018/0279954 | A1 | 10/2018 | Hayam et al. |
| 2018/0303414 | A1 | 10/2018 | Toth et al. |
| 2018/0310987 | A1 | 11/2018 | Altmann et al. |
| 2018/0311497 | A1 | 11/2018 | Viswanathan et al. |
| 2018/0338722 | A1 | 11/2018 | Altmann et al. |
| 2018/0344187 | A1* | 12/2018 | Osadchy ................ A61B 5/367 |
| 2018/0344188 | A1 | 12/2018 | Govari |
| 2018/0344202 | A1 | 12/2018 | Bar-Tal et al. |
| 2018/0344251 | A1 | 12/2018 | Harlev et al. |
| 2018/0344393 | A1 | 12/2018 | Gruba et al. |
| 2018/0360534 | A1 | 12/2018 | Teplitsky et al. |
| 2018/0365355 | A1 | 12/2018 | Auerbach et al. |
| 2019/0000540 | A1 | 1/2019 | Cohen et al. |
| 2019/0008582 | A1 | 1/2019 | Govari et al. |
| 2019/0015007 | A1 | 1/2019 | Rottmann et al. |
| 2019/0030328 | A1 | 1/2019 | Stewart et al. |
| 2019/0053708 | A1 | 2/2019 | Gliner |
| 2019/0059766 | A1 | 2/2019 | Houben et al. |
| 2019/0069950 | A1 | 3/2019 | Viswanathan et al. |
| 2019/0069954 | A1 | 3/2019 | Cohen et al. |
| 2019/0117111 | A1 | 4/2019 | Osadchy et al. |
| 2019/0117301 | A1 | 4/2019 | Steinke |
| 2019/0117303 | A1 | 4/2019 | Claude et al. |
| 2019/0117315 | A1 | 4/2019 | Keyes et al. |
| 2019/0125439 | A1 | 5/2019 | Rohl et al. |
| 2019/0133552 | A1 | 5/2019 | Shemesh et al. |
| 2019/0142293 | A1 | 5/2019 | Solis |
| 2019/0164633 | A1 | 5/2019 | Ingel et al. |
| 2019/0167137 | A1 | 6/2019 | Bar-Tal et al. |
| 2019/0167140 | A1 | 6/2019 | Williams et al. |
| 2019/0188909 | A1 | 6/2019 | Yellin et al. |
| 2019/0201664 | A1 | 7/2019 | Govari |
| 2019/0209089 | A1 | 7/2019 | Baram et al. |
| 2019/0216346 | A1 | 7/2019 | Ghodrati et al. |
| 2019/0216347 | A1 | 7/2019 | Ghodrati et al. |
| 2019/0231421 | A1 | 8/2019 | Viswanathan et al. |
| 2019/0231423 | A1 | 8/2019 | Weinkam et al. |
| 2019/0239811 | A1 | 8/2019 | Just et al. |
| 2019/0246935 | A1 | 8/2019 | Govari et al. |
| 2019/0247050 | A1 | 8/2019 | Goldsmith |
| 2019/0298442 | A1 | 10/2019 | Ogata et al. |
| 2019/0314083 | A1 | 10/2019 | Herrera et al. |
| 2019/0328260 | A1 | 10/2019 | Zeidan et al. |
| 2019/0343580 | A1 | 11/2019 | Nguyen et al. |
| 2020/0000518 | A1 | 1/2020 | Kiernan et al. |
| 2020/0008705 | A1 | 1/2020 | Ziv-Ari et al. |
| 2020/0008869 | A1 | 1/2020 | Byrd |
| 2020/0009378 | A1 | 1/2020 | Stewart et al. |
| 2020/0015890 | A1 | 1/2020 | To et al. |
| 2020/0022653 | A1 | 1/2020 | Moisa |
| 2020/0029845 | A1 | 1/2020 | Baram et al. |
| 2020/0046421 | A1 | 2/2020 | Govari |
| 2020/0046423 | A1 | 2/2020 | Viswanathan et al. |
| 2020/0060569 | A1 | 2/2020 | Tegg |
| 2020/0077959 | A1 | 3/2020 | Altmann et al. |
| 2020/0093539 | A1 | 3/2020 | Long et al. |
| 2020/0129089 | A1 | 4/2020 | Gliner et al. |
| 2020/0129125 | A1 | 4/2020 | Govari et al. |
| 2020/0129128 | A1 | 4/2020 | Gliner et al. |
| 2020/0155224 | A1 | 5/2020 | Bar-Tal |
| 2020/0163707 | A1 | 5/2020 | Sliwa et al. |
| 2020/0179650 | A1 | 6/2020 | Beeckler et al. |
| 2020/0196896 | A1 | 6/2020 | Solis |
| 2020/0205689 | A1 | 7/2020 | Squires et al. |
| 2020/0205690 | A1 | 7/2020 | Williams et al. |
| 2020/0205737 | A1 | 7/2020 | Beeckler |
| 2020/0205876 | A1 | 7/2020 | Govari |
| 2020/0205892 | A1 | 7/2020 | Viswanathan et al. |
| 2020/0206461 | A1 | 7/2020 | Govari et al. |
| 2020/0206498 | A1 | 7/2020 | Arora et al. |
| 2020/0289197 | A1 | 9/2020 | Viswanathan et al. |
| 2020/0297234 | A1 | 9/2020 | Houben et al. |
| 2020/0297281 | A1 | 9/2020 | Basu et al. |
| 2020/0305726 | A1 | 10/2020 | Salvestro et al. |
| 2020/0305946 | A1 | 10/2020 | DeSimone et al. |
| 2020/0397328 | A1 | 12/2020 | Altmann et al. |
| 2020/0398048 | A1 | 12/2020 | Krimsky et al. |
| 2021/0015549 | A1 | 1/2021 | Haghighi-Mood et al. |
| 2021/0022684 | A1 | 1/2021 | Govari et al. |
| 2021/0045805 | A1 | 2/2021 | Govari et al. |
| 2021/0059549 | A1 | 3/2021 | Urman et al. |
| 2021/0059550 | A1 | 3/2021 | Urman et al. |
| 2021/0059608 | A1 | 3/2021 | Beeckler et al. |
| 2021/0059743 | A1 | 3/2021 | Govari |
| 2021/0059747 | A1 | 3/2021 | Krans et al. |
| 2021/0077184 | A1 | 3/2021 | Basu et al. |
| 2021/0082157 | A1 | 3/2021 | Rosenberg et al. |
| 2021/0085200 | A1 | 3/2021 | Auerbach et al. |
| 2021/0085204 | A1 | 3/2021 | Auerbach et al. |
| 2021/0085215 | A1 | 3/2021 | Auerbach et al. |
| 2021/0085387 | A1 | 3/2021 | Amit et al. |
| 2021/0093292 | A1 | 4/2021 | Baram et al. |
| 2021/0093294 | A1 | 4/2021 | Shemesh et al. |
| 2021/0093374 | A1 | 4/2021 | Govari et al. |
| 2021/0093377 | A1 | 4/2021 | Herrera et al. |
| 2021/0100612 | A1 | 4/2021 | Baron et al. |
| 2021/0113822 | A1 | 4/2021 | Beeckler et al. |
| 2021/0127999 | A1 | 5/2021 | Govari et al. |
| 2021/0128010 | A1 | 5/2021 | Govari et al. |
| 2021/0133516 | A1 | 5/2021 | Govari et al. |
| 2021/0145282 | A1 | 5/2021 | Bar-Tal et al. |
| 2021/0169421 | A1 | 6/2021 | Govari |
| 2021/0169568 | A1 | 6/2021 | Govari et al. |
| 2021/0177294 | A1 | 6/2021 | Gliner et al. |
| 2021/0177356 | A1 | 6/2021 | Gliner et al. |
| 2021/0178166 | A1 | 6/2021 | Govari et al. |
| 2021/0186363 | A1 | 6/2021 | Gliner et al. |
| 2021/0187241 | A1 | 6/2021 | Govari et al. |
| 2021/0196372 | A1 | 7/2021 | Altmann et al. |
| 2021/0196394 | A1 | 7/2021 | Govari et al. |
| 2021/0212591 | A1 | 7/2021 | Govari et al. |
| 2021/0219904 | A1 | 7/2021 | Yarnitsky et al. |
| 2021/0278936 | A1 | 9/2021 | Katz et al. |
| 2021/0282659 | A1 | 9/2021 | Govari et al. |
| 2021/0290215 | A1* | 9/2021 | Amanatullah ......... A61B 90/06 |
| 2021/0307815 | A1 | 10/2021 | Govari et al. |
| 2021/0308424 | A1 | 10/2021 | Beeckler et al. |
| 2021/0338319 | A1 | 11/2021 | Govari et al. |

FOREIGN PATENT DOCUMENTS

| | | | |
|---|---|---|---|
| EP | 0668740 | A1 | 8/1995 |
| EP | 0644738 | B1 | 3/2000 |
| EP | 0727183 | B1 | 11/2002 |
| EP | 0727184 | B1 | 12/2002 |
| EP | 2783651 | A1 | 10/2014 |
| EP | 2699151 | B1 | 11/2015 |
| EP | 2699152 | B1 | 11/2015 |
| EP | 2699153 | B1 | 12/2015 |
| EP | 2498706 | B1 | 4/2016 |
| EP | 2578173 | B1 | 6/2017 |
| EP | 3238645 | A1 | 11/2017 |
| EP | 2884931 | B1 | 1/2018 |
| EP | 2349440 | B1 | 8/2019 |
| EP | 3318211 | B1 | 12/2019 |
| EP | 3581135 | A1 | 12/2019 |
| EP | 2736434 | B1 | 2/2020 |
| EP | 3451962 | B1 | 3/2020 |
| EP | 3785612 | A1 | 3/2021 |
| EP | 3972510 | A1 | 3/2022 |
| JP | 2016185296 | A | 10/2016 |
| JP | 2018524085 | A | 8/2018 |
| JP | 2019515755 | A | 6/2019 |
| WO | 9421167 | A1 | 9/1994 |
| WO | 9421169 | A1 | 9/1994 |
| WO | WO9605768 | | 2/1996 |
| WO | 9625095 | A1 | 8/1996 |
| WO | 9634560 | A1 | 11/1996 |
| WO | 0182814 | B1 | 5/2002 |
| WO | 2004087249 | A2 | 10/2004 |
| WO | 2012100185 | A2 | 7/2012 |
| WO | 2013052852 | A1 | 4/2013 |

(56) References Cited

FOREIGN PATENT DOCUMENTS

| | | | |
|---|---|---|---|
| WO | 2013162884 | A1 | 10/2013 |
| WO | 2013173917 | A1 | 11/2013 |
| WO | 2013176881 | A1 | 11/2013 |
| WO | 2014022379 | A1 | 2/2014 |
| WO | 2014176205 | A1 | 10/2014 |
| WO | 2015200518 | A1 | 12/2015 |
| WO | 2016019760 | A1 | 2/2016 |
| WO | 2016044687 | A1 | 3/2016 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2020026217 | A1 | 2/2020 |
| WO | 2020206328 | A1 | 10/2020 |
| WO | 2021119479 | A1 | 6/2021 |

OTHER PUBLICATIONS

Partial European Search Report dated Mar. 14, 2022, from corresponding European Application No. 21201890.7.

Extended European Search Report dated Jun. 14, 2022, from corresponding European Application No. 21201890.7.

Search Report dated Feb. 12, 2025, from corresponding Japanese Application No. 2021166673.

Notice of Reasons for Refusal dated Feb. 18, 2025, from corresponding Japanese Application No. 2021166673.

Written Opinion dated May 12, 2025, from corresponding Japanese Application No. 2021166673.

Decision to Grant Patent dated May 27, 2025, from corresponding Japanese Application No. 2021166673.

* cited by examiner

CATHETER AND TISSUE USING TRANSMITTER AND RECEIVERS OF THE CATHETER

FIELD OF THE INVENTION

The present invention relates generally to medical devices, and particularly to methods and systems for estimating contact force applied between catheter and tissue.

BACKGROUND OF THE INVENTION

Various techniques for measuring and/or estimating contact force between a medical device and tissue and relative positions thereof are known in the art.

For example, U.S. Patent Application Publication 2020/0206461 describes a system that includes an expandable distal-end assembly, a proximal position sensor, a distal position sensor, and a processor. The expandable distal-end assembly is coupled to a distal end of a shaft for insertion into a cavity of an organ of a patient. The proximal and distal position sensors are located at a proximal end and a distal end of the distal-end assembly, respectively. The processor is configured to estimate a position and a longitudinal direction of the proximal sensor, and a position of the distal sensor, all in a coordinate system used by the processor. The processor is further configured to project the estimated position of the distal sensor on an axis defined by the estimated longitudinal direction, and calculate an elongation of the distal-end assembly by calculating a distance between the estimated position of the proximal sensor and the projected position of the distal sensor.

U.S. Patent Application Publication 2018/0076336 describes systems, devices and methods that integrate stretchable or flexible circuitry, including arrays of active devices for enhanced sensing, diagnostic, and therapeutic capabilities. The invention enables conformal sensing contact with tissues of interest, such as the inner wall of a lumen, the brain, or the surface of the heart. Such direct, conformal contact increases accuracy of measurement and delivery of therapy. Further, the invention enables the incorporation of both sensing and therapeutic devices on the same substrate allowing for faster treatment of diseased tissue and fewer devices to perform the same procedure.

SUMMARY OF THE INVENTION

An embodiment of the present invention that is described herein provides a system including a catheter and a processor. The catheter includes an expandable distal-end assembly (EDEA) having: (i) a transmitter, which is coupled to the EDEA and is configured to transmit a first signal, and (ii) one or more receivers, which are coupled to an elastic component of the EDEA, and are configured to produce one or more respective second signals in response to receiving the first signal. The processor is configured to estimate, based on the one or more respective second signals, a force applied to the elastic component.

In some embodiments, the EDEA includes a basket, the elastic component includes one or more splines of the basket, the force includes a contact force applied between the EDEA and tissue of an organ, and in response to applying the contact force, at least one of the splines is configured to deform for conforming with a shape of the tissue. In other embodiments, the transmitter is coupled to a rigid component of the EDEA. In yet other embodiments, the rigid component includes an irrigation apparatus or a shaft of the catheter.

In an embodiment, the processor is configured to: (i) hold a calibration dataset for quantifying a relation between at least one of the respective second signals and a level of deformation of at least one of the splines, and (ii) estimate the contact force based on at least one of the respective second signals and the calibration set. In another embodiment, the processor is configured to produce the calibration set before insertion of the EDEA into the organ, and to estimate the contact force when the EDEA is placed in contact with the tissue. In yet another embodiment, when the EDEA is in an expanded position, the one or more respective second signals include: (i) a first given signal received from a given receiver of the one or more receivers without applying the contact force, and (ii) a second given signal received from the given receiver when the contact force is applied, and the processor is configured to estimate the contact force based on the first and second given signals.

In some embodiments, the EDEA includes a balloon, and the elastic component includes a member of the balloon. In other embodiments, the force includes a contact force applied between the member and tissue of an organ, and in response to applying the contact force, the member is configured to deform for conforming with a shape of the tissue, and the processor is configured to: (i) hold a calibration dataset for quantifying a relation between at least one of the respective second signals and a level of deformation of at least a section of the member, and (ii) estimate the contact force based on at least one of the respective second signals and the calibration set.

There is additionally provided, in accordance with an embodiment of the present invention, a method including inserting into an organ of a patient a catheter including an expandable distal-end assembly (EDEA) a having: (i) transmitter, which is coupled to the EDEA for transmitting a first signal, and (ii) one or more receivers, which are coupled to an elastic component of the EDEA for producing one or more respective second signals in response to receiving the first signal. The first signal is applied to the transmitter and the one or more respective second signals are received. Based on the one or more respective second signals, a force applied to the elastic component is estimated.

There is further provided, in accordance with an embodiment of the present invention, a method for producing a catheter, the method includes coupling, to an expandable distal-end assembly (EDEA) of a catheter, a transmitter for transmitting a first signal. One or more receivers for producing one or more respective second signals in response to receiving the first signal, are coupled to an elastic component of the EDEA. At least the one or more receivers are electrically coupled to a processor for receiving the one or more respective second signals and for estimating, based on the one or more respective second signals, a force applied to the elastic component.

In some embodiments, the EDEA includes a basket, the elastic component includes one or more splines of the basket, the force includes a contact force applied between the EDEA and tissue of an organ, and in response to applying the contact force, at least one of the splines is configured to deform for conforming with a shape of the tissue. In other embodiments, the transmitter is coupled to a rigid component of the EDEA, and the rigid component includes a shaft or an irrigation apparatus of the catheter. In yet other embodiments, coupling the one or more receivers includes coupling a given receiver to a given spline of the basket.

In an embodiment, the EDEA includes a balloon, and the elastic component includes a member of the balloon. In another embodiment, the force includes a contact force applied between the member and tissue of an organ, in response to applying the contact force, the member is configured to deform for conforming with a shape of the tissue.

The present invention will be more fully understood from the following detailed description of the embodiments thereof, taken together with the drawings in which:

DETAILED DESCRIPTION OF EMBODIMENTS

Overview

Figure 1:
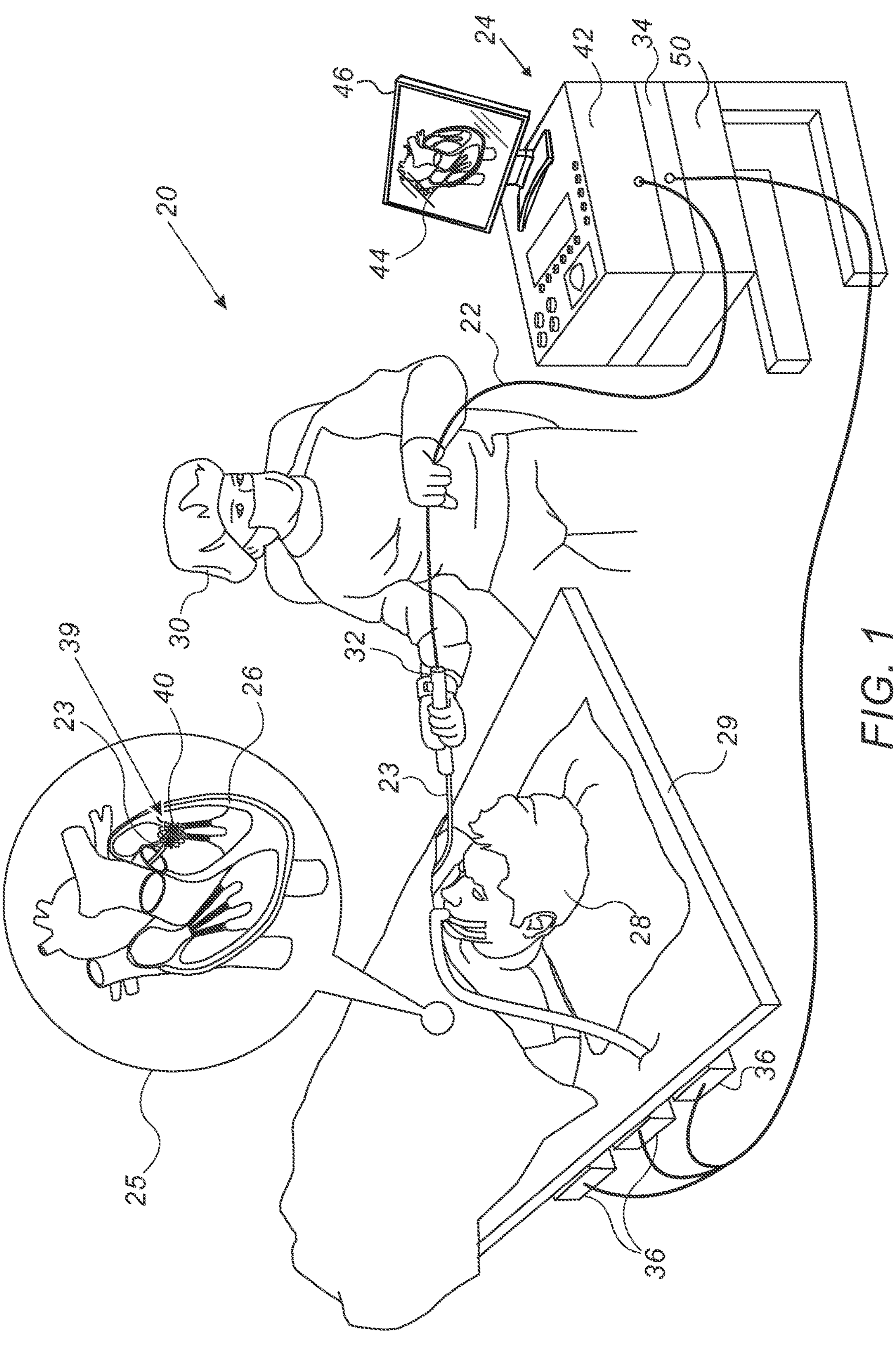
FIG. 1 is a schematic, pictorial illustration of a catheter-based position-tracking and ablation system, in accordance with an embodiment of the present invention.

Some medical procedures, such as radiofrequency (RF) ablation of tissue in a patient heart, require controlled contact force between ablation electrodes of an ablation catheter inserted into a patient heart and the heart tissue intended to be ablated by applying RF signals to the ablation electrodes. The ablation electrodes may be coupled to flexible splines of a basket-shaped expandable distal-end assembly. During the ablation procedure the distal-end assembly is inserted into the heart and expanded to an expanded position for exposing the ablation electrodes to the tissue. Some of the splines are placed in contact with the tissue and are deformed in order to conform with the tissue and for placing the electrodes in contact with the tissue intended to be ablated. The controlled contact force between the respective splines and the tissue is important for properly ablating the tissue and for producing, in the tissue in question, a lesion having specified properties.

In principle, it is possible to couple to the distal-end assembly, a device for measuring the contact force. For example, the device may include one or more piezoelectric crystals that output voltage in response to sensing contact force applied to the splines. However, the piezoelectric crystals may increase the complexity of the catheter and may provide insufficient accuracy of the measured or estimated contact force, inter alia, due to the flexibility of the splines.

Embodiments of the present invention that are described hereinbelow provide improved techniques for estimating the contact force applied, during an ablation procedure, between tissue in question (e.g., of a patient heart) and an expandable distal-end assembly (EDEA) of a catheter. Note that the improved techniques rely on quantifying and using the elastic properties of a flexible component of the distal-end assembly.

In some embodiments, a system for performing RF ablation to tissue in question comprises a catheter and a processor. The catheter comprises an EDEA having a transmitter and one or more receivers, typically implemented in electrical coils. The transmitter is coupled to a rigid component of the EDEA, e.g., a shaft or an irrigation apparatus of the catheter. The one or more receivers are coupled to respective elastic component(s) of the EDEA. For example, (i) in an EDEA comprising a basket, one or more receiver(s) may be coupled to each spline of the basket, and (ii) in an EDEA comprising a balloon, the one or more receivers may be disposed and fitted at several positions on the outer surface of the balloon.

In some embodiments, the one or more receivers are electrically connected to the processor and the transmitter is electrically connected to the processor or to a pulse generator controlled by the processor. In some embodiments, the electrical connection may be carried out using (i) electrical wires or traces running between the proximal and distal ends of the catheter, e.g., between the EDEA and an operating console of the system that comprises the processor, or (ii) wirelessly, using wireless devices coupled to the proximal and distal ends of the catheter.

In some embodiments, the processor is configured to apply to the transmitter a transmission signal, referred to herein as a first signal, and at least one of the receivers is configured to produce a receiving signal, referred to herein as a second signal, in response to receiving the first signal.

In some embodiments, during the ablation procedure, a physician inserts the EDEA into the patient heart, expands the EDEA to an expanded position, places the EDEA in contact with the tissue and applies contact force to the elastic component (e.g., splines) for performing the ablation. The processor is configured to estimate, based on the second signal received from the receiver, the contact force applied to the respective one or more splines. Note that the intensity of the first signal sensed by the receiver is proportional to the distance between the transmitter and the respective receiver. In some embodiments, in response to the contact force applied by the physician, a given spline of the splines deforms, and the deformation is sensed by the altered intensity of the first signal sensed by the respective receiver.

In some embodiments, the processor is configured to hold a calibration dataset (e.g., a calibration table) for quantifying the relation between the one or more second signals and the level of deformation of the one or more respective splines. The calibration process may be carried out as part of the manufacturing process of the EDEA, or before inserting the catheter into the patient heart.

In other embodiments, after expanding the EDEA and before placing the EDEA in contact with the heart tissue, the physician may control the processor to: (i) apply the first signal using the transmitter, and (ii) receive the one or more second signal(s) for obtaining a reference before applying the contact force to the splines. In such embodiments, after placing the EDEA in contact with the tissue and applying the contact force to the splines, the processor is configured to reapply the first signal and to receive an additional second signal. The processor is configured to estimate the contact force applied to the respective splines using the received second signals before and after applying the contact force to the splines.

The disclosed techniques improve the quality of RF ablation procedures by improving the accuracy and reducing the complexity of sensing contact force applied between ablation electrodes and tissue intended to be ablated during the RF ablation procedure. The disclosed techniques are also applicable, mutatis mutandis, to any other medical procedure that requires accurate sensing of contact force between a medical device pressed against tissue.

System Description

FIG. 1 is a schematic, pictorial illustration of a catheter-based position-tracking and ablation system 20, in accordance with an embodiment of the present invention. In some embodiments, system 20 comprises a catheter 22, in the present example an expandable cardiac catheter, and a control console 24. In the embodiment described herein, catheter 22 may be used for any suitable therapeutic and/or diagnostic purposes, such as ablation of tissue in a heart 26 and for mapping cardiac arrhythmias by sensing intra-cardiac electrical signals.

In some embodiments, console 24 comprises a processor 42, typically a general-purpose computer, with suitable front end and interface circuits for receiving signals from catheter 22 and for controlling other components of system 20 described herein. Processor 42 may be programmed in software to carry out the functions that are used by the system, and is configured to store data for the software in a memory 50. The software may be downloaded to console 24 in electronic form, over a network, for example, or it may be provided on non-transitory tangible media, such as optical, magnetic or electronic memory media. Alternatively, some or all of the functions of processor 42 may be carried out using an application-specific integrated circuit (ASIC) or any suitable type of programmable digital hardware components.

Reference e is now made to an inset 25. In some embodiments, catheter 22 comprises an expandable distal-end assembly 40 having multiple splines (shown in detail in FIG. 2 below), and a shaft 23 for inserting distal-end assembly 40 to a target location for ablating tissue in heart 26. During an ablation procedure, physician 30 inserts catheter 22 through the vasculature system of a patient 28 lying on a table 29. Physician 30 moves distal-end assembly 40 to the target location in heart 26 using a manipulator 32 near a proximal end of catheter 22, which is connected to interface circuitry of processor 42.

In some embodiments, catheter 22 comprises a position sensor 39 of a position tracking system, which is coupled to the distal end of catheter 22, e.g., in close proximity to distal-end assembly 40. In the present example, position sensor 39 comprises a magnetic position sensor, but in other embodiments, any other suitable type of position sensor (e.g., other than magnetic-based) may be used.

Reference is now made back to the general view of FIG. 1. In some embodiments, during the navigation of distal-end assembly 40 in heart 26, processor 42 receives signals from magnetic position sensor 39 in response to magnetic fields from external field generators 36, for example, for the purpose of measuring the position of distal-end assembly 40 in heart 26. In some embodiments, console 24 comprises a driver circuit 34, configured to drive magnetic field generators 36. Magnetic field generators 36 are placed at known positions external to patient 28, e.g., below table 29.

In some embodiments, processor 42 is configured to display, e.g., on a display 46 of console 24, the tracked position of distal-end assembly 40 overlaid on an image 44 of heart 26.

The method of position sensing using external magnetic fields is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of medical systems and procedures.

Figure 2:
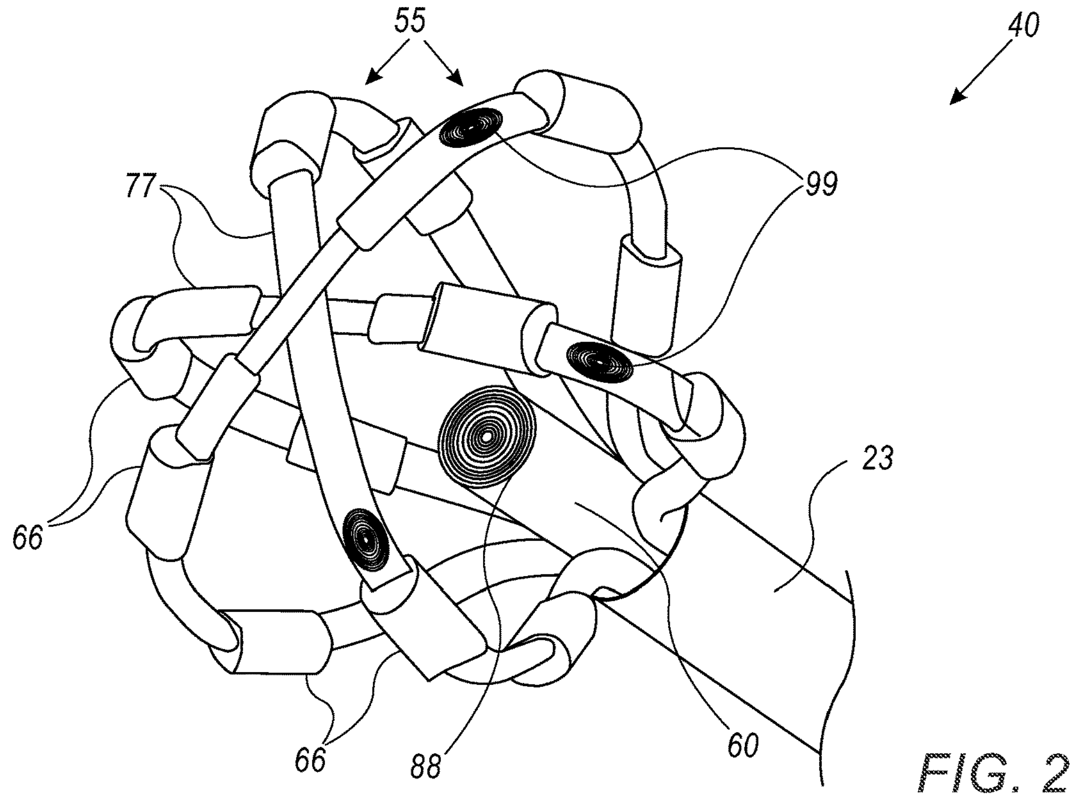
FIG. 2 is a schematic, pictorial illustration of a distal-end assembly of a catheter of the system depicted in FIG. 1, in accordance with an embodiment of the present invention.

Distal-End Assembly Having Transmitter and Receivers for Measuring Contact Force FIG. 2 is a schematic, pictorial illustration of distal-end assembly 40 in an expanded position, in accordance with an embodiment of the present invention.

In some embodiments, distal-end assembly 40 comprises multiple splines 55 of a basket-shaped assembly. Each spline 55 comprises a flexible arm 77 made from a suitable elastic substance, such as but not limited to a flexible printed circuit board (PCB), or a suitable biocompatible and flexible metal alloy (e.g., nickel-titanium based, such as nitinol) that may be partially coated with one or more electrically insulating layer(s) to prevent electrical shorts between splines 55.

In some embodiments, one or more ablation electrodes 66 are coupled to each spline 55 and are configured to apply ablation pulse(s) to tissue of heart 26. The ablation pulse(s) are intended to kill cells of the tissue in question and to produce, instead of the tissue, a lesion that prevents or reduces the propagation of electrophysiological (EP) waves through the ablated tissue.

In some embodiments, distal-end assembly 40 comprises a transmitter 88 and one or more receivers 99. Transmitter 88 is coupled to a rigid component of distal-end assembly 40, in the present example, transmitter 88 is coupled to an irrigation apparatus, also referred to herein as an irrigator 60, which is configured to apply irrigation fluid when applying the ablation signals to tissue of heart 26, or at any other suitable time interval of the ablation procedure. In other embodiments, transmitter 88 may be coupled to any other suitable rigid component of distal-end assembly 40, such as shaft 23. In the context of the present disclosure and in the claims, the term "rigid" refers to a component of catheter 22 that moves together with the catheter and whose location is not affected by any force, such as contact force, applied to distal-end assembly 40, as will be described in detail below. In other words, transmitter 88 has the same angular velocity and the same angular acceleration of the distal end of shaft 23.

In some embodiments, one or more receivers 99 are coupled to respective elastic components of distal-end assembly 40. In the present example, distal-end assembly 40 comprises a basket having multiple splines 55, and one receiver 99 is coupled to each spline 55 of the basket. In alternative embodiments, distal-end assembly 40 may comprise a balloon (not shown) having a flexible member, or any other suitable type of expandable distal-end assembly. In case of a balloon, receivers 99 may be disposed at several positions on the outer surface of the balloon. Note that in the example of FIG. 2, only three receivers 99 are shown, but a receiver 99 is coupled to each spline 55 even though some of receivers 99 are hidden by the isometric perspective of distal-end assembly 40, and therefore, are not shown in the example configuration of FIG. 2.

In some embodiments, transmitter 88 and receivers 99 may be implemented using electrical coils that are coupled to irrigator 60 and splines 55, respectively. The coils of transmitter 88 and receivers 99 are electrically connected to console 24, and more particularly, to processor 42 using any suitable connection techniques described in detail below.

In some embodiments, receivers 99 are electrically connected (e.g., via traces of the aforementioned flexible PCB, and via catheter 22) to processor 42. Moreover, transmitter 88 is electrically connected to processor 42 (e.g., via wires running between (i) the distal end of shaft 23 or irrigator 60, and (ii) the proximal end of catheter 22). Additionally, or alternatively, transmitter 88 may be electrically connected to a pulse generator (not shown) controlled by processor 42 and configured to apply one or more pulses using transmitter 88 as will be described below.

In other embodiments, the electrical connection between (i) transmitter 88 and/or receivers 99 and (ii) processor 42, may be carried out using wireless devices (not shown) coupled to the proximal and distal ends of catheter 22.

In some embodiments, processor 42 is configured to control transmitter 88 to apply a transmission signal, also referred to herein as a first signal. In response to receiving the first signal, at least one of and typically all receivers 99, are configured to produce a receiving signal, also referred to herein as a second signal.

In some embodiments, the second signal produced by a given receiver 99 is indicative of the distance between transmitter 88 and given receiver 99, as will be described below.

In some embodiments, during the ablation procedure, physician 30 inserts distal-end assembly 40 into a cavity of heart 26. Subsequently, physician 30 expands distal-end assembly 40 to an expanded position (as shown in the example of FIG. 2), places distal-end assembly 40 in contact with the tissue intended to be ablated, and applies contact force to splines 55 (or any elastic component of another sort of expandable distal-end assembly) for performing the ablation of the tissue in heart 26.

In some embodiments, processor 42 is configured to receive the second signals from receivers 99 and to estimate, based on the second signals, the contact force applied to the respective one or more splines 55. Note that the intensity of the first signal sensed by a given receiver 99 is indicative of (e.g., proportional to) the distance between transmitter 88 and given receiver 99, the smaller the distance the larger the intensity of the first signal sensed by given receiver 99. In the present example, the sensitivity of the estimated change in distance between transmitter 88 and given receiver 99 is about 0.01 mm, whereas when applying the contact force to distal-end assembly 40 the change in distance between transmitter 88 and given receiver 99 is typically larger than about 0.1 mm.

In the context of the present disclosure and in the claims, the terms "about" or "approximately" for any numerical values or ranges indicate a suitable dimensional tolerance that allows the part or collection of components to function for its intended purpose as described herein.

In some embodiments, in response to the contact force applied to distal-end assembly 40 by physician 30, arm 77 of a given spline 55 having given receiver 99 coupled thereto is deformed, and the deformation is sensed by the altered intensity of the first signal sensed by the given receiver 99.

In some embodiments, processor 42 is configured to hold a calibration dataset (e.g., a calibration table) for quantifying the relation between the one or more second signals and the level of deformation of the one or more respective splines 55. The calibration process may be carried out as part of the manufacturing process of distal-end assembly 40, or at any other time interval before inserting distal-end assembly 40 into heart 26 of patient 28.

In some embodiments, processor 42 is configured to translate the change in distance between transmitter 88 and given receiver 99 to the contact force applied to the spline having the given receiver coupled thereto (e.g., using the calibration dataset. As described above, the sensitivity of estimating the change in distance is higher than the typical deformation of the spline. Therefore, processor 42 is configured to estimate the contact force applied to the spline with a typical sensitivity of about 5 grams also referred to herein as gram-force (GF), whereas a typical value of contact force applied in such procedures is between about 0 grams and 100 grams.

In other embodiments, after expanding distal-end assembly 40 and before placing distal-end assembly 40 in contact with the tissue in question of heart 26, physician 30 may control processor 42 to: (i) apply the first signal using transmitter 88, and (ii) receive the one or more second signal(s) from one or more respective receivers 99 for obtaining a reference before applying the contact force to splines 55. In such embodiments, after placing distal-end assembly 40 in contact with the tissue intended to be ablated, and applying the contact force to splines 55, processor 42 is configured to control transmitter 88 to reapply the first signal. Subsequently, processor 42 is configured to receive from one or more receivers 99, additional second signals.

In some embodiments, processor 42 is configured to estimate the contact force applied to the respective splines 55 using the received second signals before and after applying the contact force to the respective splines 55.

In some embodiments, processor 42 holds a threshold indicative of the minimal level of contact force, which is applicable for applying the ablation pulse(s) to the tissue in question of heart 26. In some embodiments, processor 42 controls a RF pulse generator (not shown) of system 20 to apply the RF ablation signal(s) to a given ablation electrode 66, only when the contact force estimated by processor 42 using the techniques described above, is larger than the threshold. Thus, the disclosed techniques improve the quality of RF ablation procedures by improving the accuracy of the estimated contact force applied between ablation electrodes 66 and the tissue of heart 26, which is intended to be ablated during the RF ablation procedure described above. The disclosed techniques are also applicable, mutatis mutandis, to any other medical procedure that requires accurate and stable sensing of contact force between a medical device pressed against tissue.

The configuration of distal-end assembly 40 is provided in FIG. 2 by way of example, in order to illustrate certain problems that are addressed by embodiments of the present invention and to demonstrate the application of these embodiments in enhancing the performance of such a distal end for treating arrhythmias in patient heart. Embodiments of the present invention, however, are by no means limited to this specific sort of example distal-end assembly, and the principles described herein may similarly be applied to other sorts of catheters used in any suitable sort of medical systems and procedures that require measurement or estimation of contact force applied to any suitable type of medical device pressed against any suitable tissue of a patient.

Figure 3:
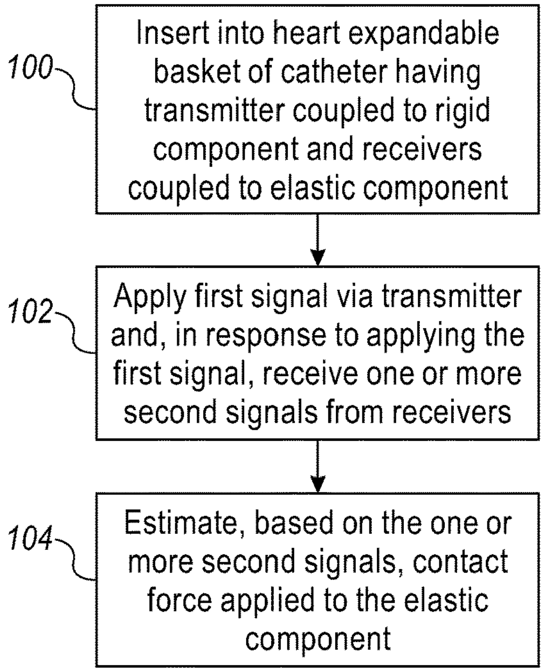
FIG. 3 is a flow chart that schematically illustrates a method for estimating a contact force applied between the distal-end assembly and tissue of a patient heart, in accordance with an embodiment of the present invention.

FIG. 3 is a flow chart that schematically illustrates a method for estimating contact force applied between distal-end assembly 40 and tissue of heart 26, in accordance with an embodiment of the present invention.

The method begins at a catheter insertion step 100, with physician 30 inserting distal-end assembly 40 of catheter 22 into a cavity of heart 26. In some embodiments, distal-end assembly 40 comprises a basket having splines 55 and ablation electrodes 66 coupled to arms 77 of splines 55.

In some embodiments, distal-end assembly 40 has transmitter 88 coupled to a rigid component of distal-end assembly 40, in the present example, irrigator 60 or the distal end of shaft 23. Distal-end assembly 40 further comprises one or more receivers 99 coupled to at least one of and typically all splines 55, which are elastic components of distal-end assembly 40 and are configured to deform in response to applying contact force between the tissue and the respective spline(s) 55, as described in FIG. 2 above.

In some embodiments, transmitter 88 is controlled by processor 42 and is configured to apply a transmitted signal, also referred to herein as the first signal, as described in FIG. 2 above. Receivers 99 are configured to produce respective second signals in response to sensing/receiving the first signal applied by transmitter 88, as also described in FIG. 2 above.

At a signal application step 102, processor 42 controls transmitter 88 to apply the first signal, and, in response to applying the first signal, processor 42 receives one or more second signals from respective receivers 99, as described in FIG. 2 above.

At a contact force estimation step 104 that concludes the method, processor 42 estimates the contact force applied to the respective one or more splines 55, based on the one or more second signals received from the one or more respective receivers 99 coupled to the one or more respective splines 55 of distal-end assembly 40.

In some embodiments, a calibration process is carried out before estimating the contact force. In the calibration process, the applied contact force and resulting deformation of splines 55 are quantified relative to the second signal produced by one or more receivers 99 coupled to one or more splines 55. In other words, after the calibration, processor 42 is configured to receive from a given receiver 99 that is coupled to a given spline 55, a given second signal, and based on the given second signal, processor 42 is configured to provide physician 30 with an estimated change in the contact force applied to given spline 55 pressed against tissue of heart 26. The calibration may be carried out in the production of distal-end assembly 40, or at any other suitable time interval before applying the contact force to one or more splines 55 of distal-end assembly 40.

Figure 4:
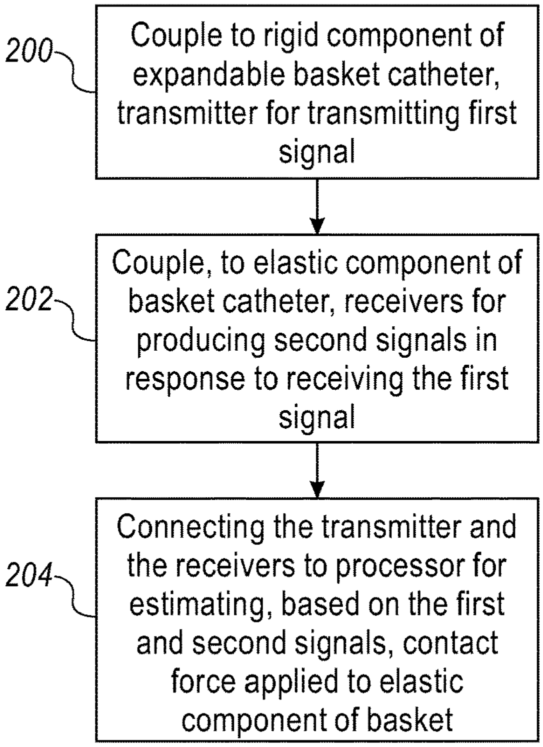
FIG. 4 is a flow chart that schematically illustrates a method for producing the distal-end assembly depicted in FIG. 2, in accordance with an embodiment of the present invention.

FIG. 4 is a flow chart that schematically illustrates a method for producing distal-end assembly 40 depicted in FIG. 2 above, in accordance with an embodiment of the present invention.

The method begins at a transmitter coupling step 200, with coupling transmitter 88 to a rigid component of catheter 22 and/or distal-end assembly 40. In the example of FIG. 2 above, the rigid component comprises an irrigation apparatus, referred to herein as irrigator 60, or the distal end of shaft 23. In other embodiments, transmitter 88 may be coupled to any other suitable rigid component of catheter 22.

In some embodiments, transmitter 88 is controlled by processor 42 and is configured to produce a first signal, as described in FIG. 2 above.

At a receiver coupling step 202, one or more receivers 99 are coupled to one or more respective elastic components (e.g., splines 55) of distal-end assembly 40. In some embodiments, in response to receiving or sensing the first signal applied by transmitter 88, receivers 99 are configured to produce a second signal indicative of the distance between transmitter 88 and the respective receiver 99.

In some embodiments, any suitable number of receivers 99 may be coupled along each spline 55, the number of coupled receivers 99 may be similar among all splines 55 or may differ between different splines 55. In one example implementation of distal-end assembly 40, one receiver 99 may be coupled to each spline 55. In another example implementation of distal-end assembly 40, multiple receivers 55 are coupled to a first spline 55, only one receiver 99 is coupled to a second spline 55, and a third spline 55 may not have any receiver 99.

At a connecting step 204 that concludes the method, transmitter 88 and receivers 99 are electrically connected to processor 42 for estimating, based on the first and second signals, the contact force applied to each spline 55 of distal-end assembly 40. The electrical connectors may comprise electrical leads or wires coupled between the distal and proximal ends of catheter 22, or electrical traces of the flexible PCB, or wireless devices coupled to the distal and proximal ends of catheter 22, as described in FIG. 2 above.

In some embodiments, after the production method may comprise additional steps, such as but not limited to: (i) coupling ablation electrodes to arms 77 of splines 55, (ii) coating one or more sections of one or more splines 55 using one or more electrically insulating layer(s), and (iii) coupling distal-end assembly 40 to catheter 22, for example by coupling splines 55 to the distal end of shaft 23 or to any other suitable component of catheter 22.

Although the embodiments described herein mainly address estimation of contact force applied between an expandable distal-end assembly of an RF ablation catheter and tissue intended to be ablated, the methods and systems described herein can also be used in other applications, such as in any application that requires accurate measurement of contact force applied between any suitable medical device and any suitable tissue of an organ of a patient. For example, in organs of an ear-nose-throat (ENT) system of a patient.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A system, comprising:

a catheter, comprising a shaft and a basket coupled to a distal end of the shaft, the basket comprising:

(i) a rigid component comprising an irrigation apparatus, (ii) a transmitter, coupled to the rigid component, such that the transmitter has a same angular velocity and a same angular acceleration of the distal end of the shaft, and is configured to transmit a first signal, (iii) an elastic component comprising a plurality of splines that are configured to deform relative to the rigid component to which the transmitter is coupled, and (iv) a plurality of receivers, which are each coupled, at different positions, to the plurality of splines, and are each configured to produce respective second signals in response to receiving the first signal, at least two splines of the plurality of splines each comprising one or more receivers of the plurality of receivers; and a processor, which is configured to estimate, based on the respective second signals, a force applied to the elastic component at the different positions of each receiver of the plurality of receivers, the force comprising a contact force applied between the basket and tissue of an organ, and in response to applying the contact force, at least one of the splines of the plurality of splines is configured to deform to conform to a shape of the tissue such that a distance between the one or more receivers of the at least one of the splines changes relative to the transmitter.

2. The system according to claim 1, wherein the processor is configured to: (i) hold a calibration dataset for quantifying a relation between at least one of the respective second signals and a level of deformation of at least one of the splines of the plurality of splines, and (ii) estimate the contact force based on at least one of the respective second signals and the calibration dataset.

3. The system according to claim 2, wherein the processor is configured to produce the calibration dataset before insertion of the basket into the organ, and to estimate the contact force when the basket is placed in contact with the tissue.

4. The system according to claim 1, wherein, when the basket is in an expanded position, each respective second signal associated with each receiver comprises: (i) a first given signal received from a given receiver of the plurality of receivers without applying the contact force, and (ii) a second given signal received from the given receiver when the contact force is applied, and wherein the processor is configured to estimate the contact force based on the first and second given signals.

5. The system of claim 1, wherein, in response to applying the contact force, a location of the rigid component is configured to be unchanged relative to a location of the distal end of the shaft.

6. A method, comprising:

inserting into an organ of a patient a catheter comprising a shaft and a basket coupled to a distal end of the shaft, the basket comprising:

(i) a rigid component comprising an irrigation apparatus, (ii) a transmitter, which is coupled to an irrigation apparatus of the basket for transmitting a first signal, (iii) an elastic component comprising a plurality of splines that are configured to deform relative to the rigid component to which the transmitter is coupled, and (iv) a plurality of receivers, which are each coupled, at different positions, to the plurality of splines for producing respective second signals in response to receiving the first signal, at least two splines of the plurality of splines each comprising one or more receivers of the plurality of receivers;

applying the first signal to the transmitter;

receiving the respective second signals of each receiver of the plurality of receivers; and estimating, based on the respective second signals, a force applied to the elastic component at the different positions of each receiver of the plurality of receivers, the force comprising a contact force applied between the basket and tissue of the organ, and in response to applying the contact force, at least one of the splines of the plurality of splines deforms to conform to a shape of the tissue such that a distance between the one or more receivers of the at least one of the splines changes relative to the transmitter.

7. The method according to claim 6, wherein estimating the force comprises: (i) holding a calibration dataset for quantifying a relation between at least one of the respective second signals and a level of deformation of at least one of the splines of the plurality of splines, and (ii) estimating the contact force based on at least one of the respective second signals and the calibration dataset.

8. The method according to claim 6, (i) and comprising, before inserting the basket into the organ, producing a calibration dataset by measuring the relation between at least one of the respective second signals and the level of deformation of a respective spline of the splines, and (ii) estimating the contact force when the basket is placed in contact with the tissue.

9. The method according to claim 6, wherein, when the basket is in an expanded position, each respective second signal associated with each receiver comprises: (i) a first given signal received from a given receiver of the one or more receivers without applying the contact force, and (ii) a second given signal received from the given receiver when the contact force is applied, and wherein estimating the force comprises estimating the contact force based on the first and second given signals.

10. The method of claim 6, wherein, in response to applying the contact force, a location of the rigid component is configured to be unchanged relative to a location of the distal end of the shaft.

11. A method for producing a catheter, the method comprising:

coupling, to an irrigation apparatus of a basket of a catheter, a transmitter for transmitting a first signal, such that the transmitter has a same angular velocity and a same angular acceleration of a distal end of a shaft of the catheter;

coupling, at different positions and to an elastic component of the basket, a plurality of receivers for producing respective second signals in response to receiving the first signal, the clastic component comprising a plurality of splines of the basket that are configured to deform relative to the irrigation apparatus to which the transmitter is coupled, at least two splines of the plurality of splines each comprising one or more receivers of the plurality of receivers; and electrically coupling at least the plurality of receivers to a processor for receiving the respective second signals and for estimating, based on the respective second signals, a force applied to the clastic component at the different positions of each receiver of the plurality of receivers, the force comprising a contact force applied between the basket and tissue of an organ, and in response to applying the contact force, at least one of the splines of the plurality of splines is configured to deform to conform to a shape of the tissue such that a distance between the one or more receivers of the at least one of the splines changes relative to the transmitter.

12. The method according to claim 11, wherein coupling the plurality of receivers comprises coupling a given receiver to a given spline of the basket.

13. The method of claim 11, wherein, in response to applying the contact force, a location of the irrigation apparatus is configured to be unchanged relative to a location of the distal end of the shaft.

* * * * *